United States Patent
Wada et al.

(12) 
(10) Patent No.: US 6,416,500 B1
(45) Date of Patent: Jul. 9, 2002

(54) DISPOSABLE URINE RETAINING BAG FOR ADULT MEN

(75) Inventors: Ichiro Wada; Kozo Abe; Noriyuki Kurita, all of Kagawa-ken (JP)

(73) Assignee: Uni-Charm Corporation, Ehime-Ken (JP)

(*) Notice: Subject to any disclaimer, the term of this patent is extended or adjusted under 35 U.S.C. 154(b) by 9 days.

(21) Appl. No.: 09/665,286

(22) Filed: Sep. 20, 2000

(30) Foreign Application Priority Data

Sep. 21, 1999 (JP) .......................... 11-267684
Nov. 18, 1999 (JP) .......................... 11-328138

(51) Int. Cl.⁷ .................................. A61F 5/44
(52) U.S. Cl. .................. 604/349; 604/346; 604/347
(58) Field of Search ................. 604/346, 347, 604/349; 4/144.1

(56) References Cited

U.S. PATENT DOCUMENTS

| | | | | |
|---|---|---|---|---|
| 3,707,969 A | * | 1/1973 | Sanford | 128/287 |
| 4,675,012 A | * | 6/1987 | Rooyakkers | 604/349 |
| 4,710,188 A | * | 12/1987 | Runeman | 604/385 |
| 4,772,280 A | | 9/1988 | Rooyakkers | |
| 5,745,926 A | * | 5/1998 | Cailleteau | 4/144.1 |
| 5,827,250 A | * | 10/1998 | Fujioka et al. | 604/349 |

FOREIGN PATENT DOCUMENTS

| | | |
|---|---|---|
| EP | 0 787 472 | 8/1997 |
| EP | 0 997 126 | 5/2000 |
| GB | 2 296 440 | 7/1996 |
| JP | 04096748 | 3/1992 |
| JP | 9-38126 | 2/1997 |
| JP | 9-38127 | 2/1997 |

* cited by examiner

Primary Examiner—John G. Weiss
Assistant Examiner—Jacqueline Stephens
(74) Attorney, Agent, or Firm—Lowe Hauptman Gilman & Berner, LLP

(57) ABSTRACT

A disposable urine retaining bag for adult man includes, a generally inverted trigonal pyramid defined by a front wall section and first and second side wall sections, the sections are formed with a liquid absorbent core and a liquid-impermeable sheet covering an outer surface of the core, the sections are foldable along longitudinal boundary lines of them, and the bag has a mouth for inserting the penis which is provided with fasteners and an elastic member.

8 Claims, 9 Drawing Sheets

DISPOSABLE URINE RETAINING BAG FOR ADULT MEN

BACKGROUND OF THE INVENTION

This invention relates to a men's disposable urine retaining bag adapted to be used, for example, bedridden patients, aged men or incontinent patients.

Japanese Patent Application Disclosure No. 1997-38126 describes a men's disposable urine holding bag dimensioned to be larger in its longitudinal direction and comprising a liquid-pervious topsheet, a liquid-impervious backsheet and a liquid-absorbent core disposed between these two sheets. The bag is formed along a part of its upper edge adjacent one end thereof with a penis insertion mouth extending through the sheets and core. The bag is torn along a guide line by an appropriate length depending on a length of the wearer's penis to form the mouth for insertion of the wearer's penis and then the penis is inserted into the bag through the mouth in actual use of the bag.

Japanese Patent Application Disclosure No. 1997-38127 describes a men's disposable urine retaining bag dimensioned to be larger in its longitudinal direction and comprising a liquid-pervious topsheet, a liquid-impervious backsheet and a liquid-absorbent core disposed between these two sheets. The bag is formed with a cutout extending downward from the upper part toward the lower part of the bag. The penis is inserted into the bag through the cutout.

With the bags described in these Japanese Patent Application Disclosure Nos. 1997-38126 and 1997-38127, the mouth or the cutout must be outstretch to define spaces within the bag so that the penis can be inserted thereinto. To achieve this, the bag must be pushed inward from transversely opposite sides of the bag so that the mouth or the cutout may be appropriately outstretched. However, the mouth or cutout, therefore, the space defined within the bag is collapsed as soon as the bag is relieved of the pressure exerted on the transversely opposite sides. This is for the reason that both of these bags have their initial shapes flattened due to join lines extending along their longitudinally opposite ends as well as transversely opposite side edges.

The glans penis must be inserted into the bag through the mouth or cutout and it is difficult to maintain the mouth or cutout in its outstretched position. As a result, an operation of inserting the penis into the bag may be delayed. Additionally, both of these bags have their plane figures which are substantially rectangular and, in consequence, the lower ends of these bags are not well fitted to the with wearer's crotch. Such may give the wearer uncomfortable feeling.

SUMMARY OF THE INVENTION

It is an object of this invention to provide a men's disposable urine retaining bag improved to ensure the space once formed within the bag to be not easily collapsed, to facilitate the penis to be inserted into the bag and to make the lower end of the bag well fit to the wearer's crotch without giving the wearer any uncomfortable feeling.

According to this invention, there is provided a men's disposable urine containing bag comprising: a generally inverted trigonal pyramid defined by a front wall section and first and second side wall sections which are formed with a liquid-absorbent panel and a liquid-impermeable sheet covering an outer surface of the liquid-absorbent panel; the bag having a first foldable line which extends along a longitudinal boundary between the front wall section and the first side wall section, a second foldable line which extends along longitudinal boundary between the front wall section and the second side wall section, and a third foldable line which extends along a longitudinal boundary between the first and second side wall sections; and a mouth for insertion of the penis defined by upper peripheral edges of the front wall section and a pair of side edges of the first and second side wall section which are separated along the third foldable line of the first and second side walls.

The men's disposable urine holding bag according to this invention enables the peripheral wall of the bag to be easily folded along the foldable lines because the regions are provided along the respective foldable lines in which the core is not present at all or, if present, the core is relatively thin and, in addition to these regions, there are provided along the foldable lines with the compressed grooves which are convex outwardly of the bag. The peripheral wall folded along the foldable lines is divided into the front wall section and the side wall sections so that these front wall section and side wall sections define the space within the bag.

The bag is provided in its front wall section with the compressed groove extending along the longitudinal center line and being convex outwardly of the bag and the elastic member extending transversely of the bag is attached to the front wall section substantially in its central zone. With such arrangement, the front wall section is normally biased to be drawn inwardly of the bag and thereby to form the space within the bag. The front wall section as well as the side wall sections are provided with the compressed grooves being convex inwardly of the bag and these compressed grooves function to prevent the space once formed within the bag from being collapsed again.

The mouth of the bag consists of the first mouth portion and the second mouth portion. Such an arrangement enables the penis to be put into the bag through said first and second mouth regions instead of inserting the penis through the mouth. In this way, the operation of inserting the penis into the bag is facilitated.

The lower part of the bag is tapered to a point so that the lower part can be received by the wearer's crotch region without any feeling of uncomfort. The bond edge of the bag is free from contact with the wearer's skin and therefore uncomfortable feeling due to the bond edge in contact with the wearer's skin is avoided. The bag is provided around the mouth with the fastening means enabling the mouth to hold the penis and preventing the penis once inserted into the bag from slipping off from the bag.

The arrangement that the upper end of the front wall section and the upper ends of the respective side wall sections are partially bonded together in the vicinity of the foldable lines is effective to avoid the apprehension that the peripheral wall of the bag might be unfolded along the foldable lines, thereby to avoid any apprehension that the bag might be flattened and the space might be collapsed.

DETAILED DESCRIPTION OF THE PREFERRED EMBODIMENTS

Details of a disposable urine retaining bag for adult man according to this invention will be more fully understood from the description given hereunder with reference to the accompanying drawings.

Figure 1:
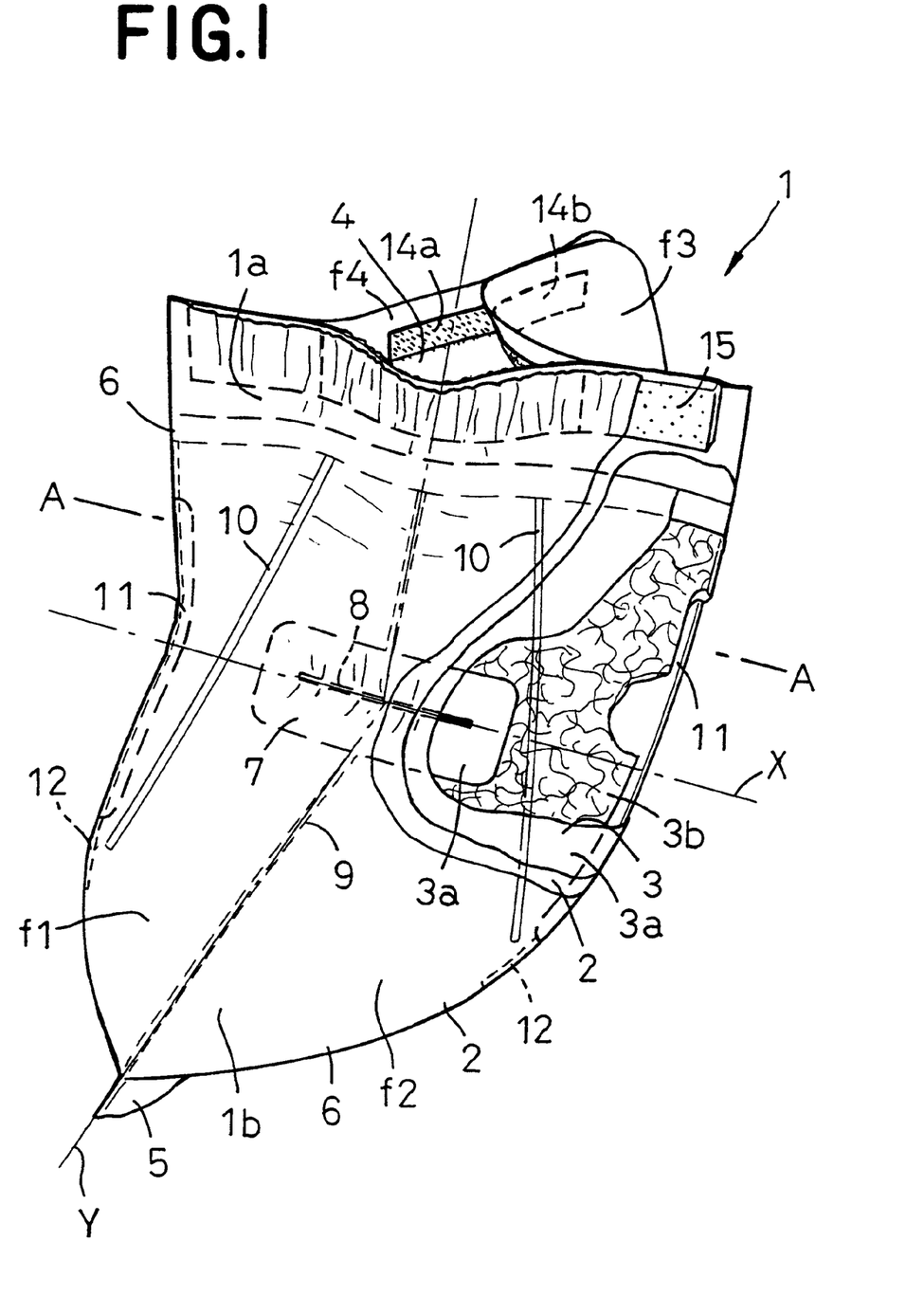
FIG. 1 is a perspective view depicting a partially cutaway disposable urine retaining bag according to this invention as viewed toward its front wall section.
Figure 2:
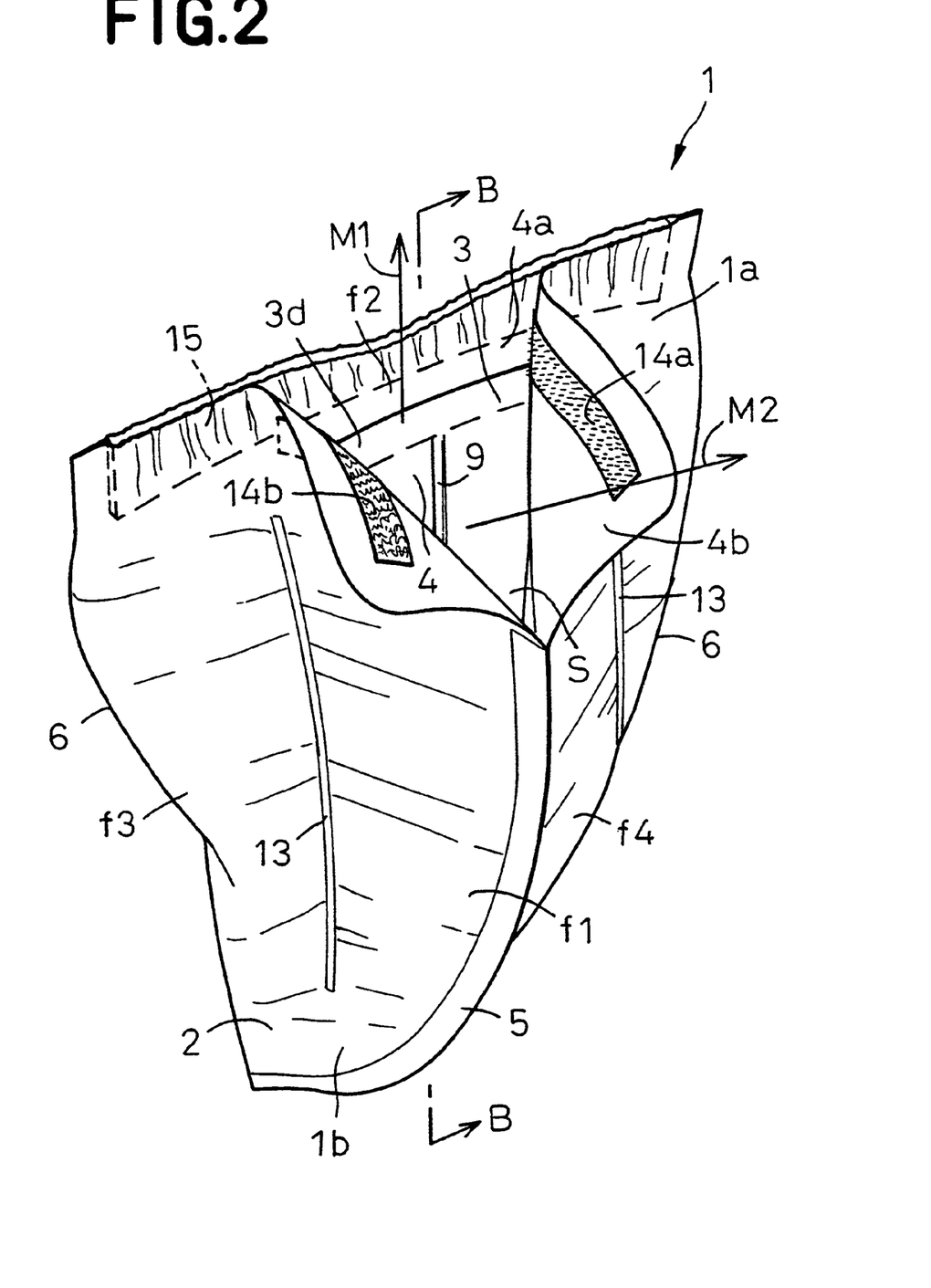
FIG. 2 is a perspective view depicting the bag of FIG. 1 as viewed toward its side wall section.

FIG. 1 is a perspective view showing a partially cutaway disposable urine retaining bag 1 according to this invention as viewed toward its front wall section f2 and FIG. 2 is a perspective view showing the bag 1 of FIG. 1 as viewed toward its side wall sections f3, f4. FIG. 2 depicts the bag 1 with its mouth 4 outstretched. The bag 1 comprises a flexible and liquid-impervious base sheet 2 serving to maintain a shape of the bag 1 and a flexible body fluid absorbent panel 3 which is attached to the inner surface of the base sheet 2 and consists of cover sheets 3a, 3a and a core 3b. The bag 1 is longitudinally tapered from its upper portion 1a toward its lower portion 1b which is, in turn, further tapered to a point. The bag 1 is provided at the uppermost end of the upper portion 1a with the mouth 4 for insertion of the wearer's penis.

The bag 1 is formed by joining the base sheet 2 along a longitudinal center line Y and bonding respective halves of the folded base sheet 2 to each other along a join edge (foldable line) 5 longitudinally extending from the upper part toward the lower part of the base sheet 2 so as to describe an arc getting near to the longitudinal center line Y. A peripheral wall f1 of the bag 1 is provided with a pair of foldable lines 6, 6 each longitudinally extending to bisect a dimension between the longitudinal center line Y and the join edge 5. Accordingly, it may be said that the bag 1 is a generally inverted trigonal pyramid in shape.

The peripheral wall f1 of the bag 1 is folded along the foldable lines 6, 6 to define a front wall section f2 extending between the pair of foldable line 6, 6 and a pair of side wall sections f3, f4 extending between the join edge 5 and the respective foldable lines 6, 6. Within the bag 1, the front wall section f2 is spaced from the pair of side wall sections f3, f4 to define a space S.

The front wall section f2 is provided substantially in its central zone with a region 7 extending transversely of the bag 1. The core 3b is absent in this region 7, i.e., the region 7 comprises parts of the base sheet 2 and the cover sheet 3a. An elastically stretchable member 8 extending transversely of the bag 1 is secured under tension to the front wall section f2 in the region 7. The region 7 in which the core 3b is absent has a rigidity lower than that of the rest region in which the core 3b is present.

A foldable line 9 which is a compressed groove formed by compressing the panel 3 in its thickness direction extending along a substantially full length of the longitudinal center line Y on the front wall section f2. In addition to the foldable line 9, the front wall section f2 is provided with a pair of foldable lines 10, 10 which are compressed grooves longitudinally extending between the longitudinal center line Y and the respective foldable line 6, 6 each formed by compressing the base sheet 2 together with the panel 3 in their thickness direction. The pair of side wall sections f3, f4 are provided with a pair of foldable lines 13, 13 which are compressed grooves longitudinally extending between the longitudinal center line Y and the respective foldable lines 6, 6 each formed by compressing the base sheet 2 together with the panel 3 in their thickness direction.

Each of the foldable lines 6, 6 is provided substantially in its middle zone with a region 11 extending along this foldable line 6. The core 3b is absent in this region 11, i.e., the region 11 comprises parts of the base sheet 2 and the cover sheet 3a. The foldable line 6 is provided substantially along its full length with a compressed groove 12 formed by compressing the panel 3 in its thickness direction.

The mouth 4 of the bag 1 comprises a first mouth portion 4a surrounded by respective upper ends of the front wall section f2 and the side wall sections f3, f4 so as to open upwardly of the bag 1 as indicated by an arrow M1 in FIG. 2 and a second mouth portion 4b surrounded by the side wall sections f3, f4 extending from the upper end of the join edge 5 toward the first mouth portion 4a so as to open laterally of the bag 1 in continuity with the first mouth portion 4a as indicated by an arrow M2 in FIG. 2. In the mouth 4, the upper end of the front wall section f2 and the respective upper ends of the side wall sections f3, f4 are partially placed upon and joined to one another in the vicinity of the foldable lines 6, 6.

In the first mouth portion 4a, an elastically stretchable member 15 extending transversely of the bag 1 is secured under tension to the front wall section f2 along its upper end and a pair of ribbon-like mechanical fasteners are attached to the respective inner surfaces of the side wall sections f3, f4 along the upper ends thereof so that these mechanical fasteners may be opposed to each other. More specifically, a hook member 14a of the mechanical fastener is attached to the side wall section f4 and a loop member 14b of the mechanical fastener is attached to the side wall section f3. These hook member 14a and loop member 14b are releasably engageable with each other so that an opening area of the first mouth region 4a may be adjusted within a range of 1~12 cm$^2$ by appropriately engaging these members 14a, 14b with each other.

Figure 3:
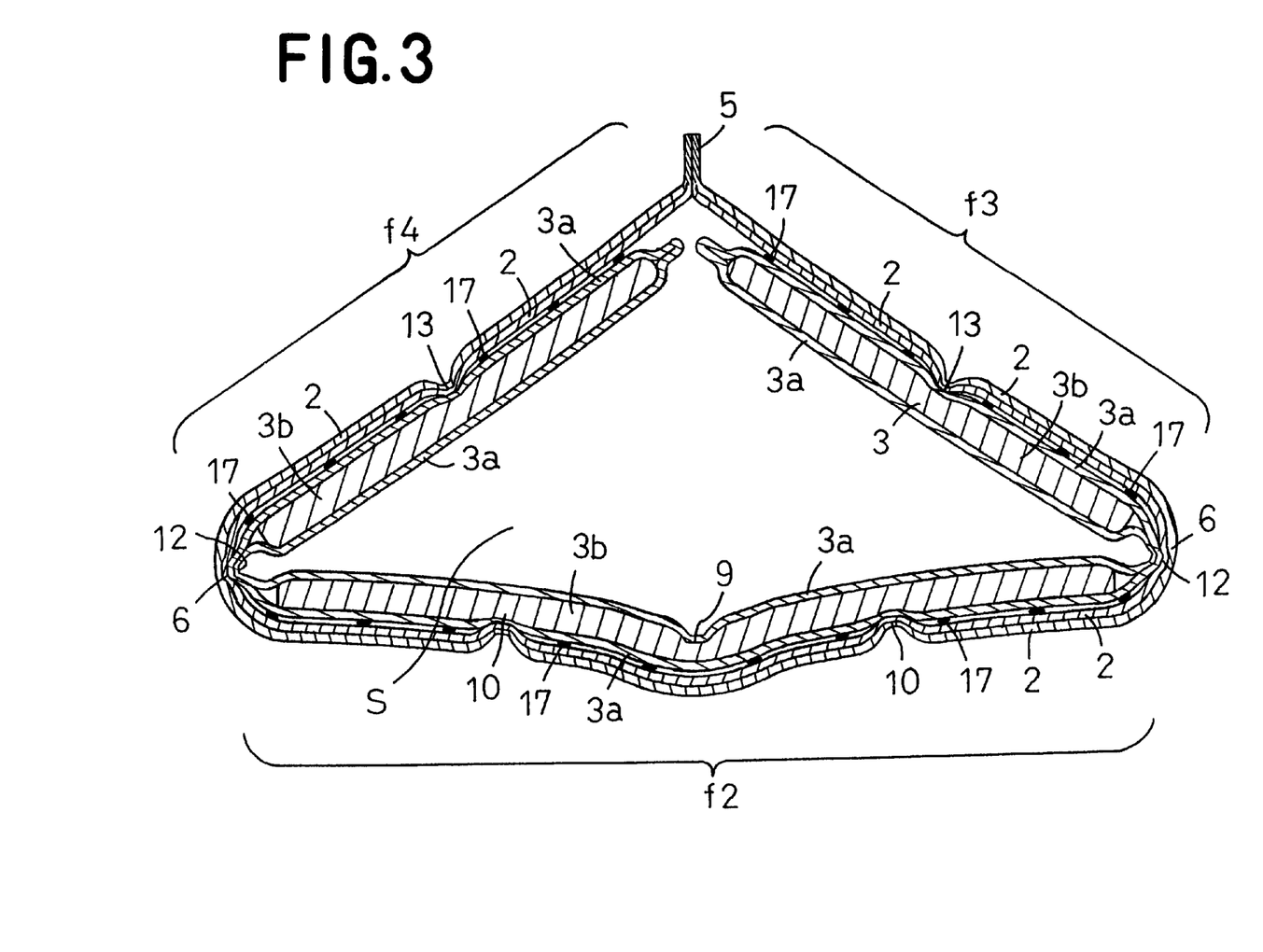
FIG. 3 is a sectional view taken along line A—A in FIG. 1.
Figure 4:
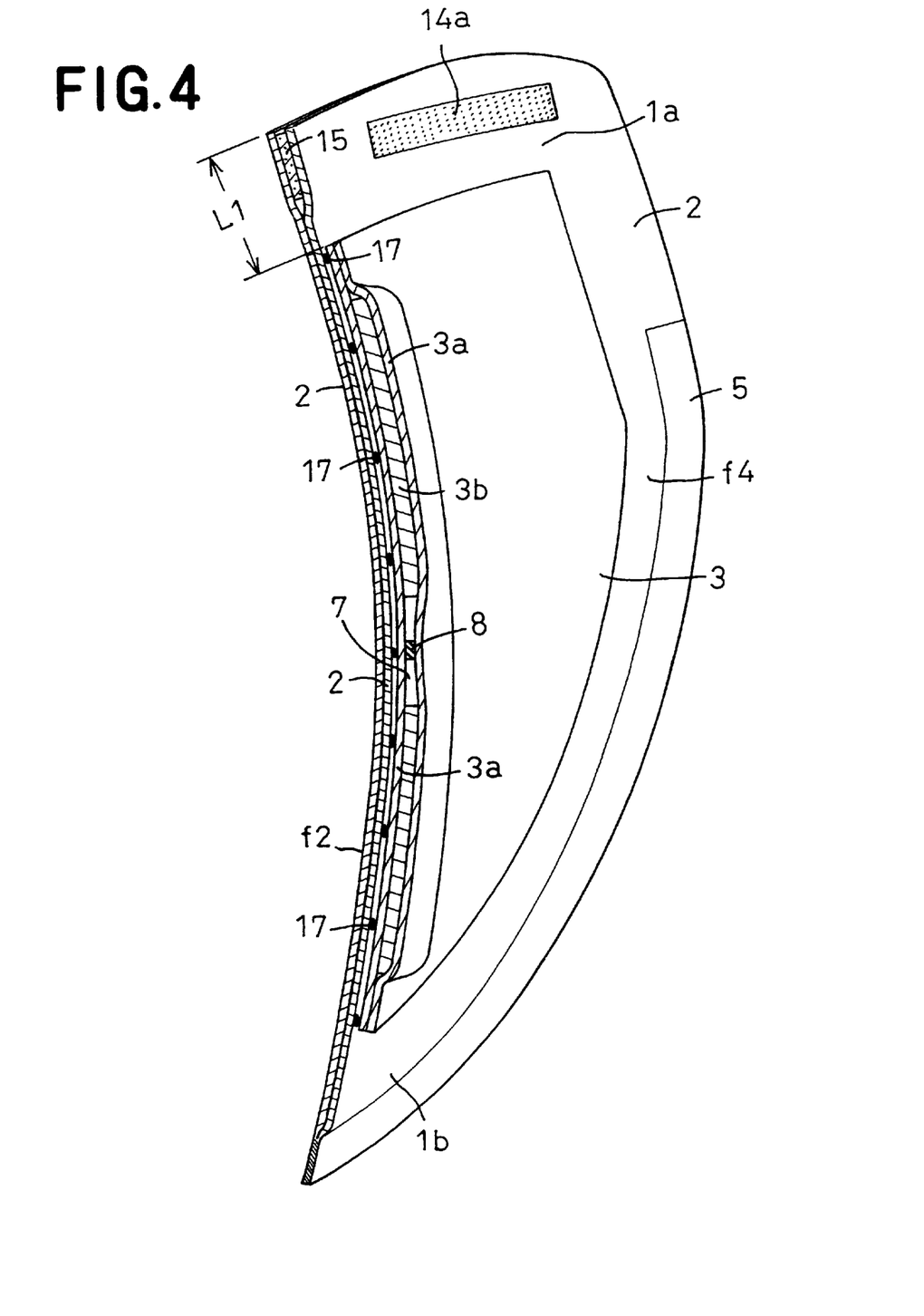
FIG. 4 is a sectional view taken along line B—B in FIG. 1.

FIG. 3 is a sectional view taken along line A—A in FIG. 1 and FIG. 4 is a sectional view taken along line B—B in FIG. 1. The base sheet 2 is two-layered and the transversely opposite side edges of the sheet 2 are put flat and joined together along the join edge 5 so that the side edges may extend upward as viewed in FIG. 3. The panel 3 comprises the semi-rigid and liquid-absorbent core 3b covered with and joined to the flexible and liquid-pervious cover sheets 3a, 3a. The cover sheets 3a, 3a are intermittently joined to the base sheet 2 by means of adhesive 17. The panel 3 occupies the front wall section f2 and the side wall sections f3, f4 except the first and second mouth portions 4a, 4b and the vicinity of the bond edge 5.

The compressed grooves 9, 12, 12 extending along the longitudinal center line Y and the respective foldable lines 6, 6 are convex outwardly of the bag 1 while the compressed grooves 10, 10, 13, 13 extending on the front wall section f2 and the respective side wall sections f3, f4 are convex inwardly of the bag 1. The elastic member 15 is disposed between the two layers of the base sheet 2 and secured under tension to the base sheet 2. The elastic member 8 is disposed between the two cover sheets 3a, 3a and secured under tension to these cover sheets 3a, 3a.

Absence of the core 3b in the regions 11, 11 of the respective foldable lines 6, 6 facilitates the peripheral wall f1 of the bag 1 to be folded along the respective foldable lines 6, 6. Similarly, absence of the core 3b in the region 7 of the front wall section f2 facilitates the front wall section f2 to be folded around a transverse center line X bisecting a longitudinal dimension of the bag 1 and thereby facilitates the bag 1 to be longitudinally curved with the front wall section f2 inside.

Contraction of the elastic member 8 attached to the bag 1 in the region 7 causes the front wall section f2 to be drawn inward transversely of the bag 1 and causes the side wall sections f3, f4 also to be drawn inward, i.e., causes the foldable lines 6, 6 to be drawn near to each other. In this way, it is possible to avoid an apprehension that the front wall section f2 might be placed against the side wall sections f3, f4 and consequently the bag 1 might be flattened.

The compressed groove 9 extending along the longitudinal center line Y and being convex outwardly of the bag 1 effectively assists the front wall section f2 to protrude outwardly of the bag 1 in the vicinity of the longitudinal center line Y. In other words, the compressed groove 9 cooperates with contraction of the elastic member 8 to facilitate the front wall section f2 to be drawn inward transversely of the bag 1.

The compressed grooves 12, 12 extending along the respective foldable lines 6, 6 and being convex outwardly of the bag 1 function to fold the peripheral wall f1 of the bag 1 so that the side wall sections f3, f4 may be drawn near to each other. In this manner, the compressed grooves 12, 12 facilitate the peripheral wall f1 of the bag 1 to be folded along the foldable lines 6, 6.

The compressed grooves 10, 10, 13, 13 longitudinally extending on the front wall section f2 and the side wall sections f3, f4, respectively, and being convex inwardly of the bag 1 function to depress the front wall section f2 inwardly of the bag 1 in the vicinity of the compressed grooves 10, 10 and to depress the side wall sections f3, f4 inwardly of the bag 1 in the vicinity of the compressed grooves 13, 13. Thus these compressed grooves 10, 10, 13, 13 prevent the space S once defined within the bag 1 from being easily collapsed again.

In the vicinity of the respective foldable lines 6, 6, the upper end of the front wall section f2 and the upper ends of the side wall sections f3, f4 are partially joined together to avoid a possibility that the peripheral wall f1 of the bag 1 might be unfolded along the foldable line 6, 6.

A dimension L1 by which the upper end of the peripheral wall f1 is spaced from the panel 3 is in a range of 5~50 mm. With the dimension L1 less than 5 mm, a movement of the bag 1 during its use may be easily transmitted to the mouth 4 and the penis P (See FIG. 6) may slip off from the mouth 4. With the dimension L1 exceeding 50 mm, the forward end of the penis P may be unable to reach the panel 3 and a urine absorbing function of the panel 3 may become useless.

Figure 5:
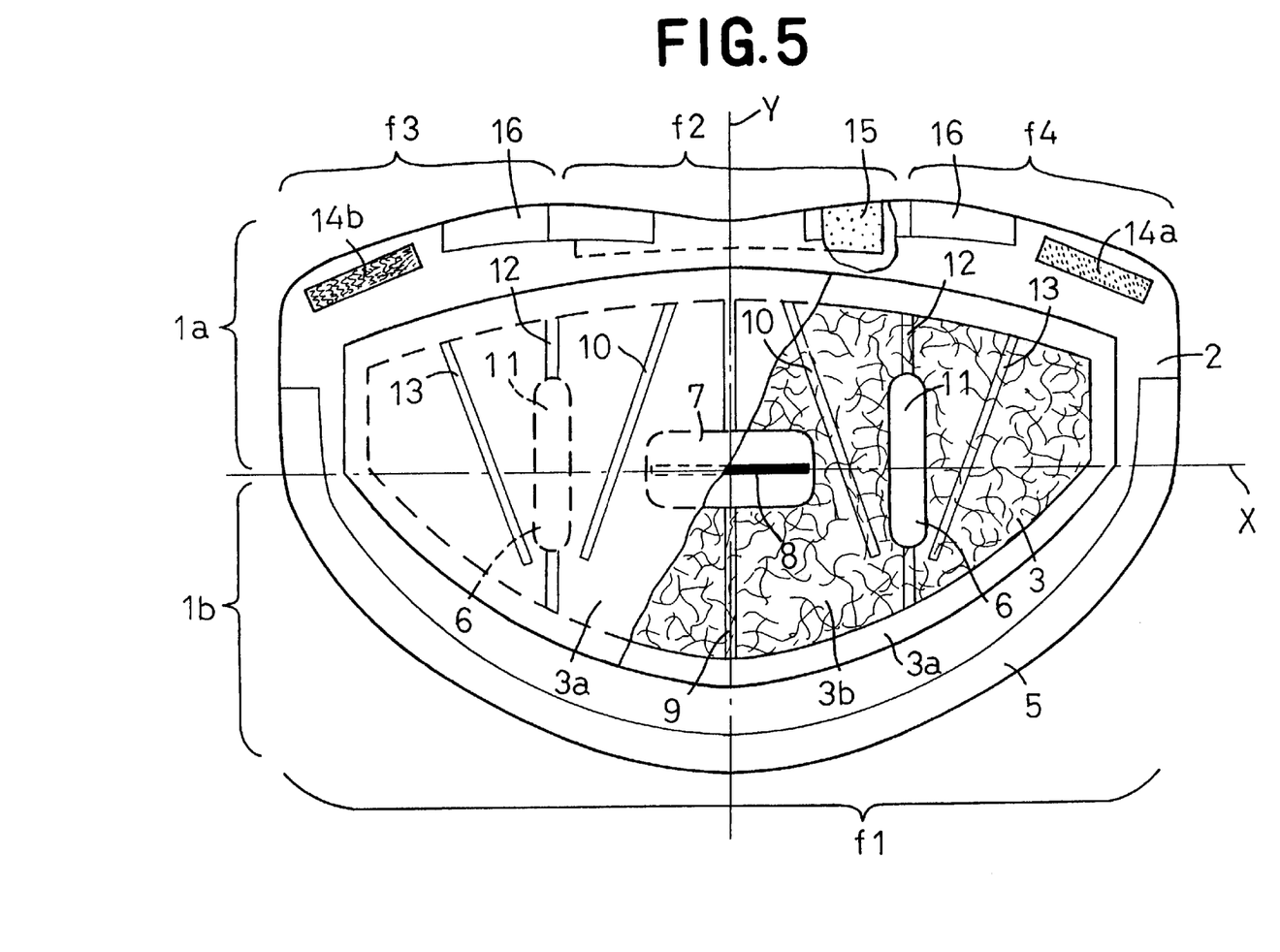
FIG. 5 is a plan view depicting the bag of FIG. 1 as developed.

FIG. 5 is a plan view showing the bag of FIG. 1 as developed. The bag 1 can be erected from the state as shown by FIG. 5 in a plan view. As will be apparent from this plan view, the panel 3 lies inside the base sheet 2 and a peripheral edge of the sheet 2 extends outward beyond a peripheral edge of the panel 3.

The peripheral edge of the base sheet 2 has its portion defining the bond edge 5 which extends downward, as viewed in FIG. 5, from the vicinity of the transverse center line X so as to describe the arc. Above the vicinity of the transverse center line X as viewed in FIG. 5, the peripheral edge of the base sheet 2 is provided with the elastic member 15 extending transversely about the longitudinally center line Y, a pair of seal zones 16, 16 extending transversely from both ends of the elastic member 15, and the hook member 14a and the loop member 14b slightly spaced transversely from the respective seal zones 16, 16.

In the panel 3, the cover sheets 3a, 3a extend outward beyond the peripheral edge of the core 3b. The panel 3 is provided along the longitudinal center line Y and the foldable lines 6, 6, respectively, the compressed groove 9 and the compressed grooves 12, 12. In addition, then pane 13 is provided with two pairs of compressed grooves 10, 13; 10, 13 each pair extending to describe a V-shape around the associated foldable line 6. The regions 11, 11 longitudinally extend substantially along middle zones of the respective foldable lines 6, 6 and the region 7 transversely extends substantially across the middle zone of the longitudinal center line Y. The elastic member 8 transversely extends in this region 7.

To erect the bag 1 from the state shown by FIG. 5 in the plan view, the base sheet 2 is folded together with the panel 3 along the longitudinal center line Y and the foldable lines 6, 6. Thereafter the halves of the base sheet 2 thus folded are bonded together along the join edge 5 and the seal zones 16, 16.

The halves of the folded base sheet 2 are left free from bonding along portions of the base sheets' peripheral edges defined between the seal zones 16, 16 and between the respective seal zones 16, 16 and the join edge 5. In this way, the bag 1 is formed with the first mouth portion 4a and the second mouth portion 4b (See FIG. 1). As viewed in FIG. 5, a section extending between the foldable lines 6, 6 defines the front wall section f2 and sections extending between the respective foldable lines 6, 6 and the bond edge 5 define the side wall sections f3, f4, respectively.

Figure 6:
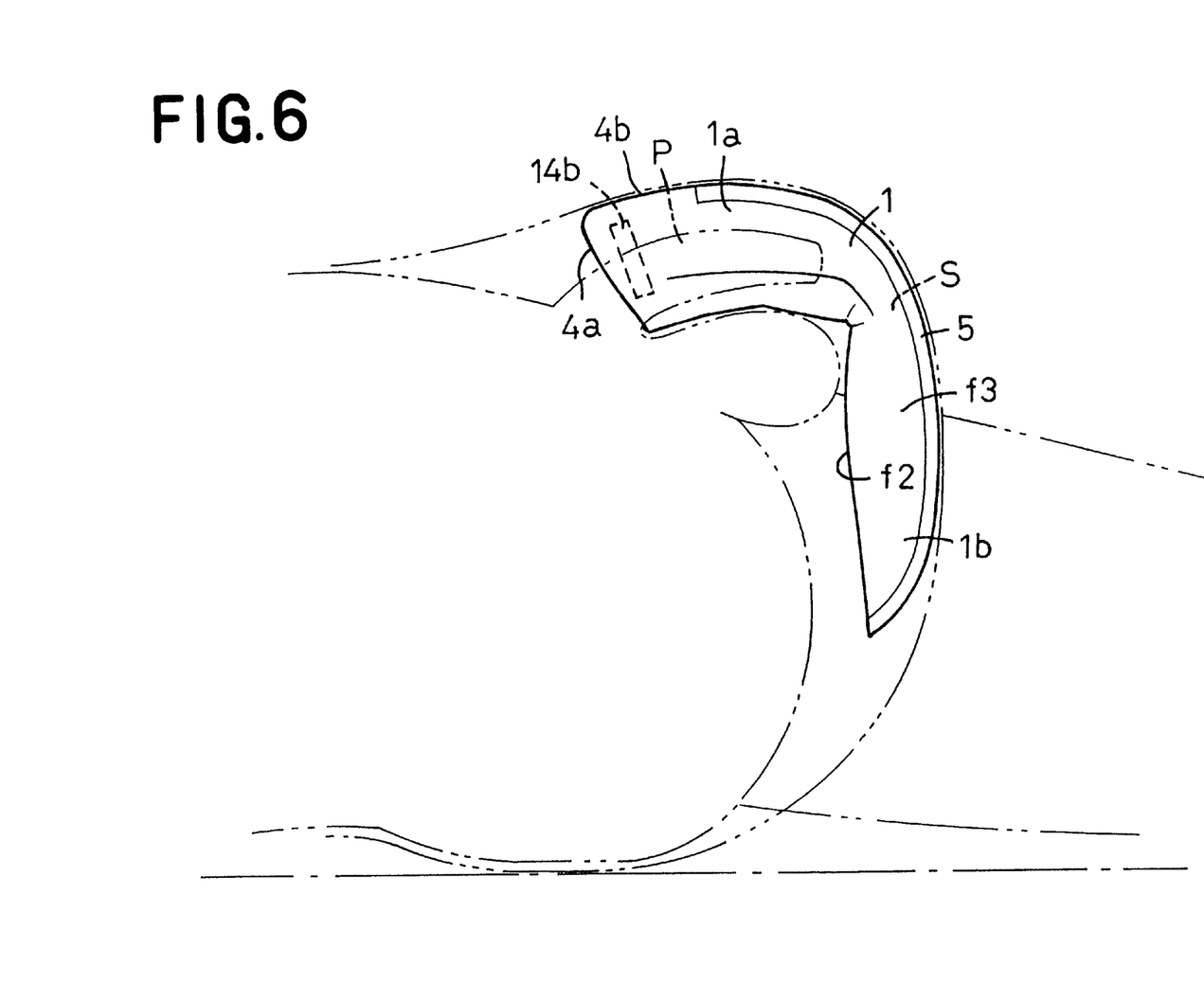
FIG. 6 is a diagram illustrating a manner in which the bag of FIG. 1 is actually used.

FIG. 6 is a diagram illustrating a manner in which the bag of FIG. 1 is actually used. The upper end of the front wall section f2 is placed around the rood of the penis P which is then put into the bag 1 through the first and second mouth regions 4a, 4b. Instead of inserting the penis P through the mouth 4, the penis P may be placed in the bag 1 via the mouth portions 4a, 4b to facilitate the operation of inserting the penis P into the bag 1. Once the penis P has been put into the bag 1, the hook member 14a and the loop member 14b attached to the side wall sections f4 and f3, respectively, are engaged with each other so that the upper ends of the side wall sections f3, f4 may wrap the penis P.

After the bag 1 has been put on the penis P, the lower part 1b of the bag 1 is positioned in the wearer's crotch region. The lower part 1b of the bag 1 positioned in the wearer's crotch region is received therein without any feeling of incompatibility since the bag 1 is tapered from the upper part 1a toward the lower part 1b which is pointed. Specifically, it is the front wall section f2 of the bag 1 but not the join edge 5 that is placed against the wearer's crotch region and therefore uncomfortable feeling due to the join edge 5 coming in contact with the wearer's skin is avoided.

Figure 7:
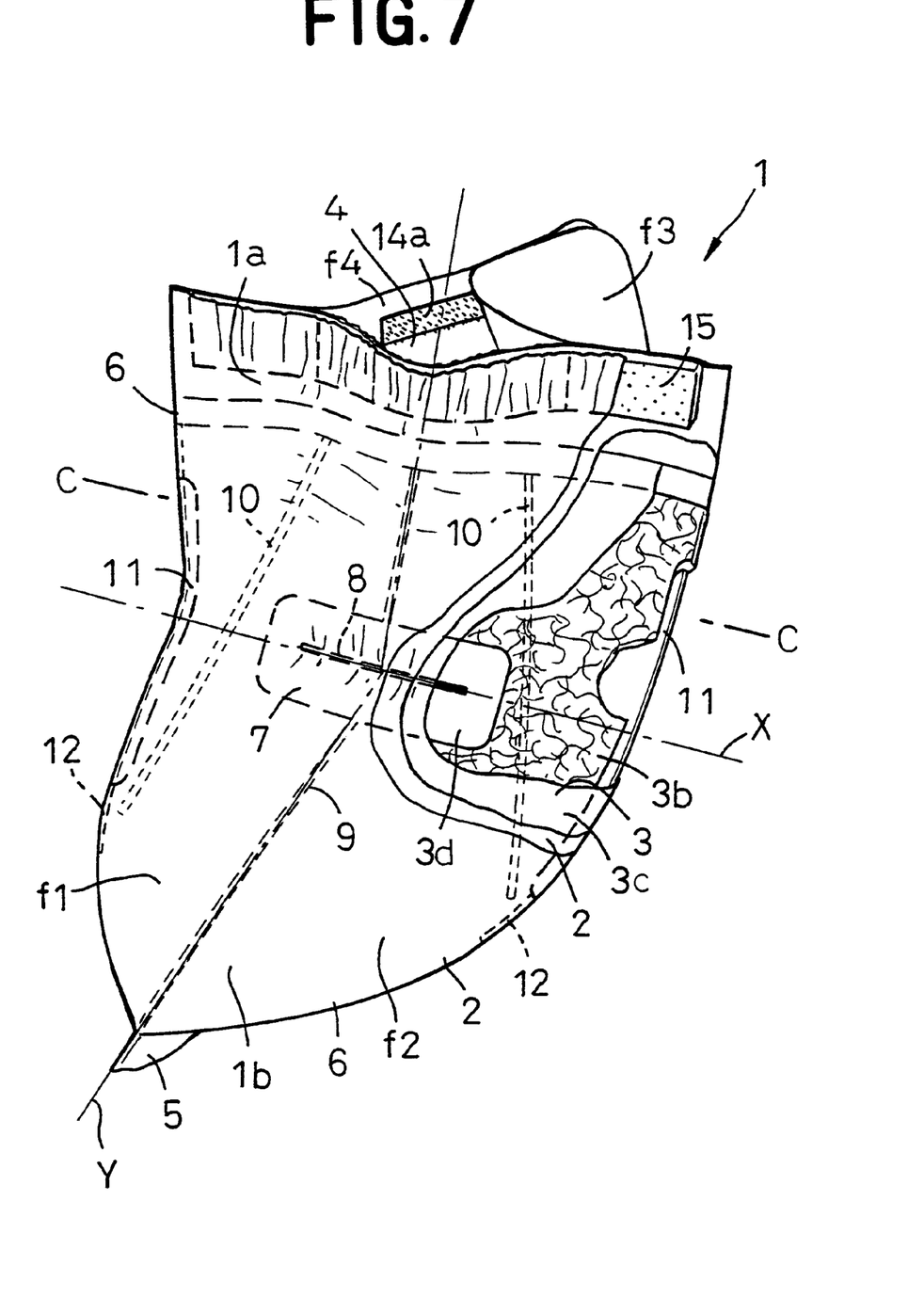
FIG. 7 is a view similar to FIG. 1 but depicting an alternative embodiment of the urine retaining bag.
Figure 8:
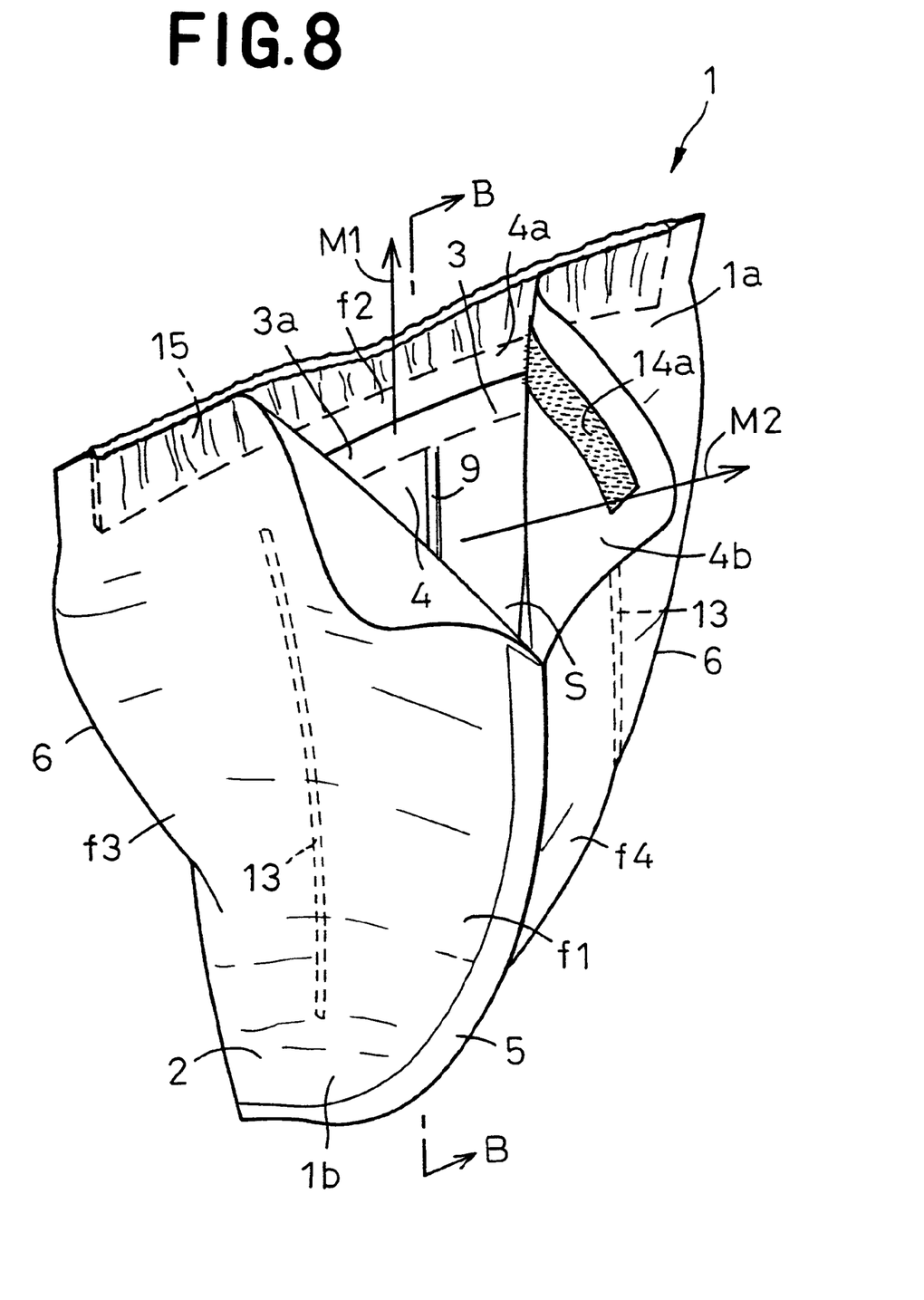
FIG. 8 is a view similar to FIG. 2 retaining the bag of FIG. 7 as viewed toward its side wall sections.

FIG. 7 is a view similar to FIG. 1 but depicting an alternative embodiment of the urine retaining bag and FIG. 8 is a view similar to FIG. 2 depicting the bag of FIG. 7 as viewed toward its side wall sections. The bag 1 comprises a flexible and liquid-impervious base sheet 2 serving to maintain a shape of the bag 1 and a flexible body fluid absorbent panel 3 which is attached to the inner surface of said base sheet 2 and consists of first and second cover sheets 3c, 3d and a core 3b. Similarly to the bag 1 shown by FIG. 1, the bag 1 according to this embodiment is longitudinally tapered from its upper portion 1a toward its lower portion 1b which is, in turn, further tapered to a point and provided at the uppermost end of the upper portion 1a with the mouth 4 for insertion of the wearer's penis.

The peripheral wall f1 of the bag 1 is folded along the foldable lines 6, 6 to define a front wall section f2 extending between the pair of foldable lines 6, 6 and a pair of side wall sections f3, f4 extending between the join edge (foldable line) 5 and the respective foldable lines 6, 6. Within the bag 1, the front wall section f2 is spaced from the pair of side wall sections f3, f4 to define a space S.

The front wall section f2 is provided substantially in its central zone with a region 7 extending transversely of the bag 1. The core 3b is absent in this region 7, i.e., the region 7 comprises parts of the base sheet 2 and the cover sheets 3c, 3d. An elastically stretchable member 8 extending transversely of the bag 1 is secured under tension to the front wall section f2 in said region 7.

A compressed groove 9 extends along a substantially full length of the longitudinal center line Y on the front wall section f2. In addition to this compressed groove 9, the front wall section f2 is provided with a pair of compressed grooves 10, 10 longitudinally extending between the longitudinal center line Y and the respective foldable lines 6, 6. The pair of side wall sections f3, f4 are provided with a pair of compressed grooves 13, 13 longitudinally extending between the longitudinal center line Y and the respective foldable lines 6, 6. These compressed grooves 9, 10, 12, 13 are formed by compressing the panel 3 in its thickness direction.

Each of the foldable lines 6, 6 is provided substantially in its middle zone with a region 11 extending along this foldable line 6. The core 3b is absent in this region 11, i.e., the region 11 comprises parts of the base sheet 2 and the cover sheet 3c, 3d.

The mouth 4 of the bag 1 comprises a first mouth portion 4a surrounded by respective upper ends of the front wall section f2 and the side wall sections f3, f4 so as to open upwardly of the bag 1 as indicated by an arrow M1 in FIG. 2 and a second mouth portion 4b surrounded by the side wall sections f3, f4 extending from the upper end of the bond edge 5 toward the first mouth portion 4a so as to open laterally of the bag 1 in continuity with the first mouth region 4a as indicated by an arrow M2 in FIG. 2. In the mouth 4, the upper end of the front wall section f2 and the respective upper ends of the side wall sections f3, f4 are partially placed upon and bonded to one another in the vicinity of the foldable lines 6, 6.

In the first mouth portion 4a, an elastically stretchable member 15 extending transversely of the bag 1 is secured under tension to the front wall section f2 along its upper end and a pair of ribbon-like mechanical fasteners are attached to the respective inner surfaces of the side wall sections f3, f4 along the upper ends thereof. More specifically, a hook member 14a of the mechanical fastener is attached to the side wall section f4 and a loop member 14b of the mechanical fastener is attached to the side wall section f3.

Figure 9:
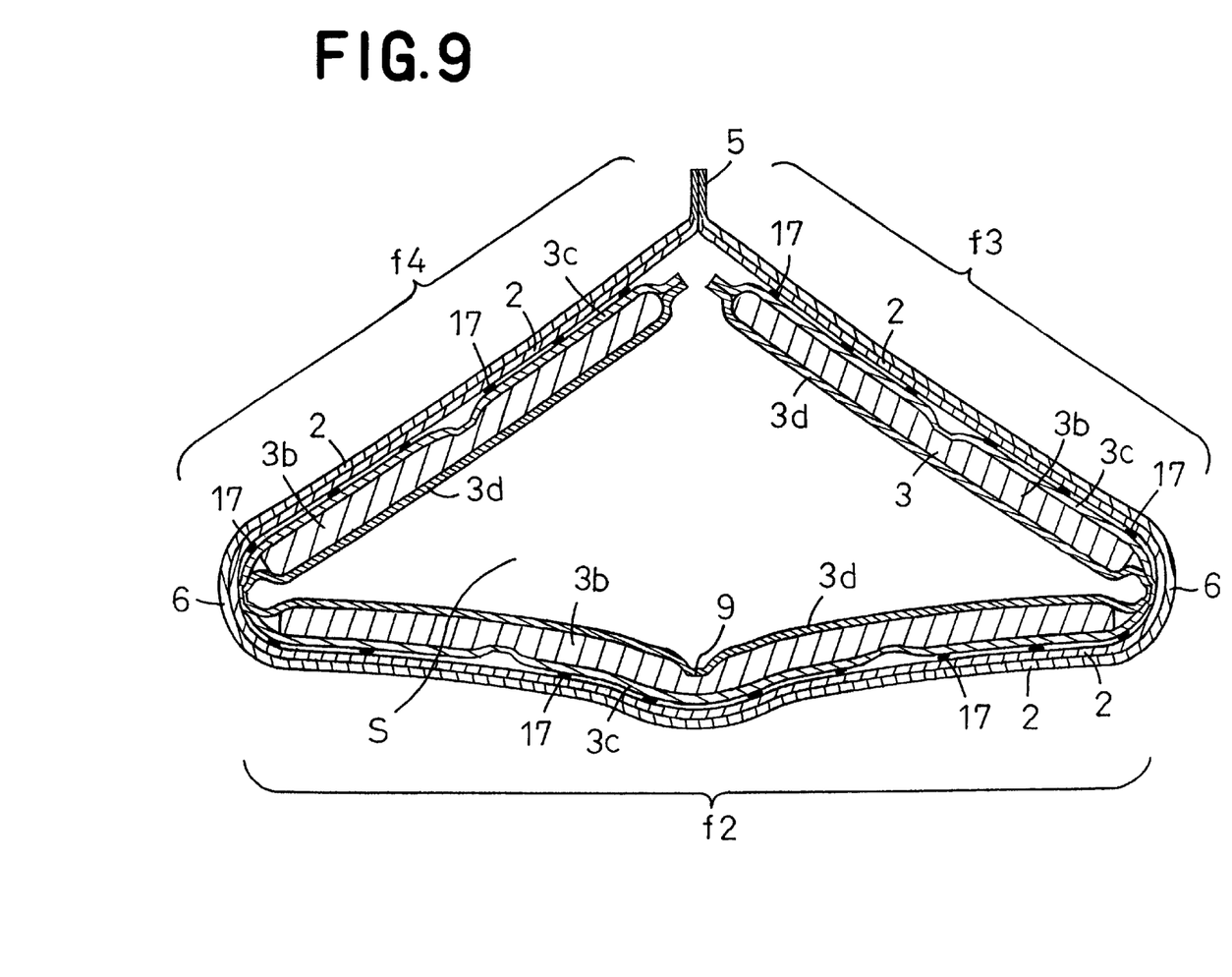
FIG. 9 is a sectional view taken along line C—C in FIG. 7.

FIG. 9 is a sectional view taken along line C—C in FIG. 7. g. The base sheet 2 is two-layered and the respective layers are joined together along the bond edge 5 extending upward as viewed in FIG. 9. The panel 3 comprises the semi-rigid and liquid-absorbent core 3b covered with and joined to the flexible and liquid-impervious first cover sheets 3c placed upon one surface of the base sheet 2 and the flexible but liquid-pervious second cover sheet 3d. The first cover sheet 3c is intermittently bonded to the base sheet 2 by means of adhesive 17. The panel 3 occupies the front wall section f2 and the side wall sections f3, f4 except the first and second mouth portions 4a, 4b and the vicinity of the bond edge 5.

The compressed grooves 9, 12, 12 extending along the longitudinal center line Y and the respective foldable lines 6, 6 are convex outwardly of the bag 1 while the compressed grooves 10, 10, 13, 13 extending on the front wall section f2 and the respective side wall sections f3, f4 are convex inwardly of the bag 1. The elastic member 15 is disposed between the two layers of the base sheet 2 and secured under tension to the base sheet 2. The elastic member 8 is disposed between the two cover sheets 3c, 3d and secured under tension to these cover sheets 3c, 3d.

To put the bag 1 of FIG. 7 on the penis P, the side wall sections f3, f4 are overlapped each other with the side wall section f4 overlying the side wall section f3 to wrap the penis P and the hook member 14a is engaged with the outer surface of the side wall section f3. In the bag 1 of FIG. 7, the liquid-impervious first cover sheet 3c placed upon the base sheet 2 prevents the amount of urine having been absorbed by the panel 3 from permeating the base sheet 2 and thereby improves a preventive effect against leakage of urine.

The base sheet 2 of the bag 1 depicted by FIG. 1 may be formed using a lamination of flexible and hydrophobic nonwoven fabric, a lamination of flexible and liquid-impervious plastic film or a laminated sheet of flexible and hydrophobic nonwoven fabric/flexible and liquid-impervious plastic film, preferably, a breathable but liquid-impervious sheet. The base sheet 2 of the bag 1 shown by FIG. 7 may be formed using a lamination of flexible and hydrophobic nonwoven fabric, or a laminated sheet of flexible and hydrophobic nonwoven fabric/flexible and liquid-impervious plastic film wherein the nonwoven fabric defines the outermost surface of the bag 1 and the plastic film lies on inner side of said nonwoven fabric.

The cover sheets 3a as well as the second cover sheet 3d may be formed using a flexible and liquid-pervious sheet such as nonwoven fabric or porous plastic film, preferably, a liquid-pervious and hydrophilic sheet. The first cover sheet 3c may be formed using flexible and hydrophobic nonwoven fabric or flexible and liquid-impervious plastic film, preferably, a breathable but liquid-impervious sheet.

The nonwoven fabric used for the purpose as has been described above may be selected from a group including air-through nonwoven fabric, spun lace nonwoven fabric, needle punch nonwoven fabric, melt blown nonwoven fabric, thermal bond nonwoven fabric, spun bond nonwoven fabric and chemical bond nonwoven fabric. The component fiber of the nonwoven fabric may be selected from a group including polyolefine, polyester, polyamide fibers and conjugated fiber such as polyethylene/polypropyrene or polyester.

The core 3b generally comprises a mixture of fluff pulp and superabsorptive hydrogel grains compressed to a desired thickness and entirely covered with a water-pervious sheet (not shown) such as tissue paper. Accordingly, the core 3b has a rigidity higher than those of the base sheet 2 and the cover sheets 3a, 3c, 3d and may be regarded as semi-rigid in comparison with said base sheet 2 and cover sheets 3a, 3c, 3d. The elastic member 15 may be formed using elastically stretchable sheet-like foam of polyurethane, synthetic rubber or polystyrene, or elastically stretchable urethane film.

Joining of the sheets 2, 3a, 3c, 3d and the core 3b as well as attaching of the elastic members 8, 15 and the mechanical fastener may be carried out using adhesive such as hot melt adhesive or pressure-sensitive adhesive or a technique of heat-sealing or ultrasonic sealing.

In the bag 1, the portions of the core 3b present in the region 7 of the front wall section f2 and the regions 11, 11 of the respective foldable lines 6, 6 may be thinner than the portion present in the rest region. These regions 7, 11, 11, in which the core 3b is relatively thin has a rigidity lower than the rest region in which the core 3b is relatively thick. As a result, the peripheral wall f1 of the bag 1 can be easily folded along the foldable lines 6, 6.

The bag 1 may be provided not only along the upper ends of the respective side wall sections f3, f4 forming the first mouth region 4a but also along the portions of the respective side wall sections f3, f4 defining the second mouth region 4b with the mechanical fasteners. An alternative arrangement is also possible that the upper end of the front wall section f2 is not bonded to the upper ends of the respective side wall sections f3, f4 in the vicinity of the foldable lines 6, 6 and the mechanical fastener members are attached to the upper end of the front wall section f2 and to the upper ends of the respective side wall sections f3, f4 in the vicinity of the foldable lines 6, 6.

The mechanical fastener members may be replaced by strips of fastening tape and retaining tape. The strip of fastening tape may be a plastic sheet having its outer surface coated with pressure-sensitive adhesive which is, in turn, protectively covered with release paper. The strip of retaining tape may be a plastic sheet with which said strip of fastening tape is releasably engaged by means of said pressure-sensitive adhesive.

The panel 3 may be provided in the form of the core 3b covered with the cover sheets 3a, 3a or with the first and second cover sheets 3c, 3d, or the core 3b disposed between the base sheet 2 and the cover sheet 3a.

Though not shown, the bag 1 is individually packaged as it is folded in two along the transverse center line X with the front wall section f2 inside. The front wall section f2 is provided with the region corresponding to the transverse center line X in which the core 3b is absent so that the region may function as a guide along which the bag 1 can be easily folded in two. In actual use, the bag 1 is taken out from the individual package and is unfolded around the transverse center line X.

What is claimed is:

1. A disposable urine retaining bag for men, said bag comprising:
   a generally inverted trigonal pyramid defined by a front wall section and first and second side wall sections which are formed with a liquid-absorbent panel and a liquid-impermeable sheet covering an outer surface of the liquid-absorbent panel;
   the bag further having a first foldable line which extends along a first longitudinal boundary between the front wall section and the first side wall section, a second foldable line which extends along a second longitudinal boundary between the front wall section and the second side wall section, and a third foldable line which extends along a third longitudinal boundary between the first and second side wall sections;
   wherein a mouth for insertion of a male wearer's penis is defined by upper edges of the front wall and first and second side wall sections and side edges of the first and second side wall sections which are separated along the third foldable line; and
   wherein a plurality of first compressed grooves, formed by compressing a thickness of said bag outwardly, extend along a longitudinal center line of said front wall section and said first and second foldable lines.

2. The bag according to claim 1, wherein said mouth is provided with fastening elements.

3. The bag according to claim 1, wherein at least one of said front wall section and said first and second side wall sections is provided along a peripheral edge of mouth with an elastically stretchable member.

4. The bag according to claim 1, wherein said panel is absent in the vicinity of a peripheral edge of said mouth.

5. The bag according to claim 1, wherein a plurality of second compressed grooves, formed by compressing the thickness of said bag inwardly, extend longitudinally in regions defined between said longitudinally center line and said first and second foldable lines, respectively, and between said first and second foldable lines and said third foldable line respectively.

6. A disposable urine retaining bag for men, said bag comprising:
   a generally inverted trigonal pyramid defined by a front wall section and first and second side wall sections which are formed with a liquid-absorbent panel and a liquid-impermeable sheet covering an outer surface of the liquid-absorbent panel;
   the bag further having a first foldable line which extends along a first longitudinal boundary between the front wall section and the first side wall section, a second foldable line which extends along a second longitudinal boundary between the front wall section and the second side wall section, and a third foldable line which extends along a third longitudinal boundary between the first and second side wall sections;
   wherein a mouth for insertion of a male wearer's penis is defined by upper edges of the front wall and first and second side wall sections and side edges of the first and second side wall sections which are separated along the third foldable line; and
   wherein said front wall section is provided in a substantially central zone thereby with a transversely extending elastically stretchable member.

7. A disposable urine retaining bag for men, said bag comprising:
   a generally inverted trigonal pyramid defined by a front wall section and first and second side wall sections which are formed with a liquid-absorbent panel and a liquid-impermeable sheet covering an outer surface of the liquid-absorbent panel;
   the bag further having a first foldable line which extends along a first longitudinal boundary between the front wall section and the first side wall section, a second foldable line which extends along a second longitudinal boundary between the front wall section and the second side wall section, and a third foldable line which extends along a third longitudinal boundary between the first and second side wall sections;
   wherein said third foldable line is a joined edge of said first and second side wall sections and said panel is not present along said third foldable line.

8. A disposable urine retaining bag for men, said bag comprising:
   a generally inverted trigonal pyramid defined by a front wall section and first and second side wall sections which are formed with a liquid-absorbent panel and a liquid-impermeable sheet covering an outer surface of the liquid-absorbent panel;
   the bag further having a first foldable line which extends along a first longitudinal boundary between the front wall section and the first side wall section, a second foldable line which extends along a second longitudinal boundary between the front wall section and the second side wall section, and a third foldable line which extends along a third longitudinal boundary between the first and second side wall sections;
   wherein a plurality of first compressed grooves, formed by compressing a thickness of said bag outwardly, extend along a longitudinal center line of said front wall section and said first and second foldable lines;
   said front wall section is provided a substantially central zone thereof with a transversely extending elastically stretchable member; and
   said third foldable line is a joined edge of said first and second side wall sections and said panel is not present along said third foldable line.

* * * * *